US008445596B2

(12) United States Patent
Mertens et al.

(10) Patent No.: US 8,445,596 B2
(45) Date of Patent: *May 21, 2013

(54) POWDERY, CROSS-LINKED ABSORBENT POLYMERS, METHOD FOR THE PRODUCTION THEREOF, AND THEIR USE

(75) Inventors: Richard Mertens, Krefeld (DE); Jörg Harren, Krefeld (DE)

(73) Assignee: Evonik Stockhausen GmbH, Krefeld (DE)

(*) Notice: Subject to any disclaimer, the term of this patent is extended or adjusted under 35 U.S.C. 154(b) by 0 days.

This patent is subject to a terminal disclaimer.

(21) Appl. No.: 11/673,137

(22) Filed: Feb. 9, 2007

(65) Prior Publication Data
US 2007/0129495 A1 Jun. 7, 2007

Related U.S. Application Data

(63) Continuation of application No. 10/455,394, filed on Jun. 6, 2003, now Pat. No. 7,179,862, which is a continuation of application No. 09/914,466, filed as application No. PCT/EP00/01609 on Feb. 26, 2000, now Pat. No. 6,620,889.

(30) Foreign Application Priority Data

Mar. 5, 1999 (DE) .................. 199 09 653

(51) Int. Cl.
C08L 33/02 (2006.01)
C08F 8/00 (2006.01)
(52) U.S. Cl.
USPC ........ 525/221; 525/329.5; 524/558; 524/559; 524/564; 526/317.1
(58) Field of Classification Search
USPC .............. 525/221, 329.5; 524/558, 559, 564; 526/317.1
See application file for complete search history.

(56) References Cited

U.S. PATENT DOCUMENTS

| | | | |
|---|---|---|---|
| 4,392,908 A | 7/1983 | Dehnel | |
| 4,771,105 A | 9/1988 | Shirai et al. | |
| 5,002,986 A * | 3/1991 | Fujiura et al. | 524/47 |
| 5,032,628 A | 7/1991 | Choi et al. | |
| 5,229,466 A | 7/1993 | Brehm et al. | |
| 5,308,701 A | 5/1994 | Cohen et al. | |
| 5,314,420 A | 5/1994 | Smith et al. | |
| 5,368,918 A | 11/1994 | Harada et al. | |
| 5,407,442 A | 4/1995 | Karapasha | |
| 5,408,019 A | 4/1995 | Mertens et al. | |
| 5,409,771 A | 4/1995 | Dahmen et al. | |
| 5,420,218 A | 5/1995 | Toribuchi et al. | |
| 5,422,405 A | 6/1995 | Dairoku et al. | |
| 5,433,753 A | 7/1995 | Dahmen et al. | |
| 5,451,613 A * | 9/1995 | Smith et al. | 521/53 |
| 5,455,284 A | 10/1995 | Dahmen et al. | |
| 5,562,646 A | 10/1996 | Goldman et al. | |
| 5,567,744 A | 10/1996 | Nagata et al. | |
| 5,575,939 A | 11/1996 | Dahmen et al. | |
| 5,599,335 A | 2/1997 | Goldman et al. | |
| 5,599,763 A | 2/1997 | Harada et al. | |
| 5,669,894 A | 9/1997 | Goldman et al. | |
| 5,672,419 A | 9/1997 | Mukaida et al. | |
| 5,684,106 A | 11/1997 | Johnson et al. | |
| 5,716,707 A | 2/1998 | Mukaida et al. | |
| 5,731,365 A | 3/1998 | Engelhardt et al. | |
| 5,840,321 A | 11/1998 | Engelhardt et al. | |
| 5,849,405 A | 12/1998 | Wang et al. | |
| 5,851,672 A | 12/1998 | Wang et al. | |
| 5,859,074 A | 1/1999 | Rezai et al. | |
| 5,954,921 A | 9/1999 | Dahmen et al. | |
| 5,985,432 A | 11/1999 | Wang et al. | |
| 5,994,440 A | 11/1999 | Staples et al. | |
| 6,001,911 A * | 12/1999 | Ishizaki et al. | 524/388 |
| 6,011,196 A | 1/2000 | Wang et al. | |
| 6,027,536 A | 2/2000 | Westerink et al. | |
| 6,060,149 A | 5/2000 | Nissing et al. | |
| 6,072,024 A | 6/2000 | Irizato et al. | |
| 6,072,101 A | 6/2000 | Beihoffer et al. | |
| 6,087,450 A | 7/2000 | Breitbach et al. | |
| 6,090,875 A | 7/2000 | Staples et al. | |

(Continued)

FOREIGN PATENT DOCUMENTS

| | | |
|---|---|---|
| AU | 6650181 A | 7/1981 |
| AU | 8744198 A | 4/1999 |

(Continued)

OTHER PUBLICATIONS

Fredric L. Buchholz and Andrew T. Graham, Modern Superabsorbent Polymer Technology, article, Copyright Dec. 1997, pp. 55-60, pp. 87-103 and pp. 252-257, Wiley-VCH.
Hirofumi Shibata, Experimental Report, report, Sep. 6, 2005, pp. 1-5.
Chemical Abstracts, vol. 127, No. 4, Jul. 28, 1997, AN 1997-316703, JP 09 124879 , May 13, 1997.
U.S. Appl. No. 09/914,466 Non Final Rejection dated Jun. 19, 2002.
U.S. Appl. No. 10/455,394 Non Final Rejected dated Oct. 19, 2004.
U.S. Appl. No. 10/455,394 Final Rejected dated Mar. 23, 2005.
U.S. Appl. No. 10/455,394 Non Final Rejected dated Aug. 10, 2005.
U.S. Appl. No. 10/455,394 Final Rejected dated Apr. 28, 2006.
Briggs, M.: "Boron Oxides, Boric Acid, and Borates" Kirk-Othmer Encyclopedia of Chemical Technology, vol. 4, 2001, pp. 259-283, XP002486769.
Database WPI Week 200425 Thomson Scientific, London, GB: AN 2004-263106 XP002486770 & JP-A-2004 097255.
Hu Z S et al.: "Study on antiwear and reducing friction additive of nanometer titanium borate" Wear Elsevier Science S.A., Lausanne, Switzerland, vol. 216, No. 1, (Mar. 15, 1998), pp. 87-91, XP002486768 NY USA.

(Continued)

Primary Examiner — Irina S Zemel
(74) Attorney, Agent, or Firm — Smith Moore Leatherwood LLP; Philip P. McCann; John P. Zimmer

(57) ABSTRACT

The invention relates to crosslinked polymerizates which are capable of absorbing, which are based on partially neutralized, monoethylenically unsaturated monomers that carry acidic groups, which exhibit improved properties, in particular, with regard to their ability to transport liquids when in a swollen state, and which have been subsequently crosslinked on the surface thereof with a combination consisting of an organic crosslinker compound, with the exception of polyols, and of a cation provided in the form of a salt in an aqueous solution.

17 Claims, No Drawings

U.S. PATENT DOCUMENTS

| | | | |
|---|---|---|---|
| 6,099,950 | A | 8/2000 | Wang et al. |
| 6,121,509 | A | 9/2000 | Ashraf et al. |
| 6,124,391 | A | 9/2000 | Sun et al. |
| 6,133,369 | A | 10/2000 | Houben et al. |
| 6,228,930 | B1 * | 5/2001 | Dairoku et al. ............... 524/500 |
| 6,229,062 | B1 | 5/2001 | Mandell et al. |
| 6,245,693 | B1 | 6/2001 | Gagliardi et al. |
| 6,297,335 | B1 | 10/2001 | Funk et al. |
| 6,323,252 | B1 | 11/2001 | Gartner et al. |
| 6,375,644 | B2 | 4/2002 | Mizutani |
| 6,376,011 | B1 | 4/2002 | Reeves et al. |
| 6,414,214 | B1 | 7/2002 | Engelhardt et al. |
| 6,423,046 | B1 | 7/2002 | Fujioka et al. |
| 6,441,266 | B1 | 8/2002 | Dyer et al. |
| 6,495,612 | B1 | 12/2002 | Corzani et al. |
| 6,498,201 | B1 | 12/2002 | Corzani et al. |
| 6,534,561 | B1 | 3/2003 | Corzani et al. |
| 6,534,572 | B1 | 3/2003 | Ahmed et al. |
| 6,602,950 | B1 | 8/2003 | Dentler et al. |
| 6,603,055 | B2 | 8/2003 | Mitchell et al. |
| 6,605,673 | B1 * | 8/2003 | Mertens et al. ............ 525/329.5 |
| 6,620,889 | B1 * | 9/2003 | Mertens et al. ............... 525/221 |
| 6,623,576 | B2 | 9/2003 | Mitchel et al. |
| 6,623,834 | B1 | 9/2003 | Nissing et al. |
| 6,716,514 | B2 | 4/2004 | Nissing |
| 6,730,057 | B2 | 5/2004 | Zhao et al. |
| 6,831,122 | B2 | 12/2004 | Daniel et al. |
| 6,867,345 | B2 | 3/2005 | Shimoe et al. |
| 7,179,862 | B2 * | 2/2007 | Mertens et al. ............... 525/221 |
| 2001/0049514 | A1 | 12/2001 | Dodge, II et al. |
| 2002/0039869 | A1 | 4/2002 | Achille |
| 2002/0045869 | A1 | 4/2002 | Dodge, II et al. |
| 2002/0090453 | A1 | 7/2002 | Muthiah et al. |
| 2002/0128618 | A1 | 9/2002 | Frenz et al. |
| 2003/0012928 | A1 | 1/2003 | Malowaniec et al. |
| 2003/0040729 | A1 | 2/2003 | Malowaniec et al. |
| 2003/0065296 | A1 | 4/2003 | Kaiser et al. |
| 2003/0088220 | A1 | 5/2003 | Molander et al. |
| 2003/0093051 | A1 | 5/2003 | Malowaniec et al. |
| 2003/0109628 | A1 | 6/2003 | Bonfanti et al. |
| 2003/0125684 | A1 | 7/2003 | Qin |
| 2003/0134552 | A1 | 7/2003 | Mehawej et al. |
| 2003/0157318 | A1 | 8/2003 | Brehm et al. |
| 2003/0175418 | A1 | 9/2003 | Muthiah et al. |
| 2003/0207639 | A1 | 11/2003 | Lin |
| 2003/0219594 | A1 | 11/2003 | Qin et al. |
| 2004/0001937 | A1 | 1/2004 | Nissing et al. |
| 2004/0054343 | A1 | 3/2004 | Barnett et al. |
| 2004/0058159 | A1 | 3/2004 | Gagliardi et al. |
| 2004/0077796 | A1 | 4/2004 | Daniel et al. |
| 2004/0078015 | A1 | 4/2004 | Copat et al. |
| 2004/0121681 | A1 | 6/2004 | Lindsay et al. |
| 2004/0180998 | A1 | 9/2004 | Gonzales et al. |
| 2004/0214499 | A1 | 10/2004 | Qin et al. |
| 2004/0214946 | A1 | 10/2004 | Smith et al. |
| 2004/0222553 | A1 | 11/2004 | Desai et al. |
| 2004/0236295 | A1 | 11/2004 | Muthiah et al. |
| 2005/0013992 | A1 | 1/2005 | Azad et al. |
| 2005/0027268 | A1 | 2/2005 | Qin et al. |
| 2005/0043696 | A1 | 2/2005 | Schmidt et al. |
| 2005/0065237 | A1 | 3/2005 | Schmidt et al. |
| 2005/0096435 | A1 | 5/2005 | Smith et al. |
| 2005/0245684 | A1 | 11/2005 | Daniel et al. |
| 2006/0025030 | A1 | 2/2006 | Funk et al. |
| 2006/0173431 | A1 | 8/2006 | Laumer et al. |
| 2006/0173432 | A1 | 8/2006 | Laumer et al. |
| 2006/0173433 | A1 | 8/2006 | Laumer et al. |
| 2007/0135554 | A1 | 6/2007 | McInstosh et al. |
| 2007/0244283 | A1 | 10/2007 | Riegel et al. |
| 2008/0021130 | A1 | 1/2008 | McIntosh et al. |
| 2008/0234420 | A1 | 9/2008 | Smith et al. |

FOREIGN PATENT DOCUMENTS

| | | | |
|---|---|---|---|
| CA | 2154425 | A1 | 1/1996 |
| CA | 2180590 | A1 | 1/1997 |
| CA | 2303298 | A1 | 3/1999 |
| CA | 2273507 | A1 | 12/1999 |
| CA | 2291997 | A1 | 6/2000 |
| CA | 2293864 | A | 6/2000 |
| CA | 2414197 | A1 | 1/2002 |
| DE | 2222780 | | 11/1973 |
| DE | 35 03 458 | | 8/1985 |
| DE | 40 20 780 | | 8/1991 |
| DE | 44 18 818 | A1 | 1/1995 |
| DE | 43 33 056 | C2 | 3/1995 |
| DE | 196 46 484 | A1 | 5/1997 |
| DE | 197 16 657 | A1 | 10/1998 |
| DE | 19939662 | | 2/2001 |
| DE | 10010269 | C1 | 7/2001 |
| EP | 0 233 067 | | 8/1987 |
| EP | 0 317 106 | A2 | 5/1989 |
| EP | 0339461 | A1 | 11/1989 |
| EP | 0 349 240 | A2 | 1/1990 |
| EP | 0372981 | A2 | 6/1990 |
| EP | 0478150 | A2 | 4/1992 |
| EP | 0 574 260 | | 12/1993 |
| EP | 0575143 | A2 | 12/1993 |
| EP | 0612533 | A1 | 8/1994 |
| EP | 0668080 | A2 | 8/1995 |
| EP | 744435 | A1 | 11/1996 |
| EP | 0744967 | A1 | 12/1996 |
| EP | 0850617 | A1 | 7/1998 |
| EP | 0612533 | B1 | 11/1999 |
| EP | 0963760 | A1 | 12/1999 |
| EP | 0 752 892 | B1 | 7/2001 |
| EP | 1259205 | A1 | 11/2002 |
| EP | 1259206 | A1 | 11/2002 |
| EP | 1259207 | A1 | 11/2002 |
| EP | 1350869 | A1 | 10/2003 |
| EP | 1354926 | | 10/2003 |
| EP | 1359240 | A1 | 11/2003 |
| EP | 1402905 | A1 | 3/2004 |
| EP | 1433450 | A1 | 6/2004 |
| EP | 1503812 | A1 | 2/2005 |
| FR | 2838445 | A1 | 10/2003 |
| GB | 9011250 | | 7/1990 |
| JP | 2242858 | | 9/1990 |
| JP | 6-15574 | | 1/1994 |
| JP | 6-107846 | | 4/1994 |
| JP | 6-298841 | | 10/1994 |
| JP | 7-33818 | | 2/1995 |
| JP | 7-310021 | | 11/1995 |
| JP | 9-124879 | | 5/1997 |
| JP | 09-510889 | | 11/1997 |
| JP | 2002-52754 | A | 8/2002 |
| JP | 2002/346381 | | 12/2002 |
| JP | 2004097255 | | 4/2004 |
| JP | 2004/298384 | | 10/2004 |
| WO | 9118042 | A1 | 11/1991 |
| WO | 9526209 | A1 | 10/1995 |
| WO | WO 96/05234 | | 2/1996 |
| WO | 9614885 | A1 | 5/1996 |
| WO | 9617884 | A1 | 6/1996 |
| WO | 9718889 | A1 | 5/1997 |
| WO | 9845466 | A1 | 10/1998 |
| WO | 9925745 | | 5/1999 |
| WO | 9957201 | A1 | 11/1999 |
| WO | 0022018 | | 4/2000 |
| WO | 0046260 | | 8/2000 |
| WO | 0055245 | | 9/2000 |
| WO | 0062922 | A1 | 10/2000 |
| WO | 03043670 | A1 | 5/2003 |
| WO | 03092757 | | 11/2003 |
| WO | 03104543 | | 12/2003 |
| WO | 03106162 | | 12/2003 |
| WO | 2004009683 | | 1/2004 |
| WO | 2004018005 | A1 | 3/2004 |
| WO | 2004018006 | A1 | 3/2004 |
| WO | 2004024816 | | 3/2004 |
| WO | 2004096301 | | 11/2004 |
| WO | 2004098475 | A1 | 11/2004 |
| WO | 2005011860 | | 2/2005 |
| WO | 2005014067 | A1 | 2/2005 |
| WO | 2005094749 | | 10/2005 |
| WO | 2005097881 | | 10/2005 |
| WO | 2006082188 | | 8/2006 |

| WO | 2006082189 | 8/2006 |
| WO | 2006082197 | 8/2006 |
| WO | 2007070262 A2 | 6/2007 |
| WO | 2007070776 A2 | 6/2007 |

OTHER PUBLICATIONS

International Search Report completed on Jul. 3, 2008 in PCT/US2007/089033.

International Search Report Mailed Jul. 21, 2008 in PCT/US2007/089033.

International Search Report mailed on Jun. 11, 2007 in PCT/US2006/061859.

Invitation to Pay Additional Fees and, Where Applicable, Protest Fee mailed on Jun. 5, 2008 in PCT/US2007/089033.

Jacqueline, I. Kroschwitz, Concise Encyclopedia of Polymer Science and Engineering, book, 1990, pp. 213-219, John Wiley & Sons, Inc.

Malcolm P. Stevens, Polymer Chemistry An Introduction, book, 1990, pp. 3-12, Second Edition, Oxford University Press, New York, New York.

Written Opinion of the International Searching Authority mailed on Jun. 11, 2007 in PCT/US2006/061859.

Written Opinion of the International Searching Authority mailed on Jul. 21, 2008 in PCT/US2007/089033.

* cited by examiner

POWDERY, CROSS-LINKED ABSORBENT POLYMERS, METHOD FOR THE PRODUCTION THEREOF, AND THEIR USE

This application is a continuation of application Ser. No. 10/455,394, filed Jun. 6, 2003, now U.S. Pat. No. 7,179,862, which is a continuation of application Ser. No. 09/914,466 filed Aug. 29, 2001, now U.S. Pat. No. 6,620,889, which was the National Stage of International Application No. PCT/EP00/01609 filed Feb. 26, 2000, which claims the benefit of German Application No. 199 09 653.8 filed Mar. 5, 1999.

The invention relates to powdered, crosslinked polymers (superabsorbers) which absorb water, aqueous liquids, as well as blood, and have improved properties, particularly improved retention and improved liquid retention capability under pressure and an improved capability of conveying liquids, and to their production and their use as absorbents in hygiene articles and in technical fields.

Superabsorbers are water-insoluble, crosslinked polymers capable of absorbing large amounts of aqueous liquids and body fluids such as urine or blood with swelling and formation of hydrogels, and retaining them under a specific pressure. As a result of these characteristic properties, these polymers are predominantly used for incorporation in sanitary articles, e.g., in diapers for babies, incontinence articles, or in liners.

Essentially, the superabsorbers commercially available at present are crosslinked polyacrylic acids or crosslinked starch/acrylic acid graft polymers wherein the carboxyl groups are partially neutralized with sodium hydroxide or potassium hydroxide solution.

For aesthetic reasons and from environmental-aspects, there is an increasing tendency of designing sanitary articles such as diapers for babies, incontinence articles and liners increasingly smaller and thinner. In order to ensure a constant retention capability of the sanitary articles, the above requirement can only be realized by reducing the percentage of large-volume fluff. As a result, the superabsorber also has to assume functions with respect to conveyance and distribution of liquid, which may be summarized as permeability properties.

Permeability in the case of a superabsorber material is understood to be the ability of conveying added liquids and distributing them in a three-dimensional fashion in its swollen state. In a swollen superabsorber gel, this process takes place via capillary conveyance through interstices between the gel particles. The actual conveyance of liquid through swollen superabsorber particles complies with the laws of diffusion and is an exceedingly slow process which, in the service condition of the sanitary article, does not play any role in the distribution of liquid. In superabsorber materials incapable of accomplishing capillary conveyance due to lacking gel stability, separation of the particles from each other has been ensured by embedding these materials in a fiber matrix, thereby avoiding the gel blocking phenomenon. In new generation diaper constructions, the absorber layer has only minor amounts of fiber material to support the conveyance of liquid, or none at all. Accordingly, the superabsorbers used therein must have sufficiently high stability in their swollen state, so that the swollen gel still has a sufficient quantity of capillary space, through which conveyance of liquid is possible.

In one aspect, in order to obtain superabsorber materials having high gel strength, the polymer crosslinking level could be increased, which would inevitably result in a loss of swelling capacity and retention capability. Indeed, an optimized combination of various crosslinkers and comonomers as described in the patent specification DE 196 46 484 is able to improve the permeability properties, but not to such a level that incorporation in a diaper construction of a layer optionally consisting of superabsorbers only would be possible.

Furthermore, methods of surface secondary crosslinking or the polymer particles may be used. During the so-called secondary crosslinking, the carboxyl groups of the polymer molecules at the surface of the superabsorber particles are reacted with various secondary crosslinking agents capable of reacting with at least two of the carboxyl groups near the surface. In addition to increasing the gel strength, the capability of absorbing liquids under pressure is highly improved in particular, because the well-known phenomenon of gel blocking is suppressed, where slightly swollen polymer particles adhere to each other, thereby preventing further absorption of liquid.

The surface treatment of liquid-absorbing resins is already well-known. To improve the dispersibility, ionic complexing of the carboxyl groups near the surface using polyvalent metal cations has been suggested in U.S. Pat. No. 4,043,952. This treatment is effected using salts of multivalent metals dispersed in organic solvents (alcohols and other organic solvents) optionally containing water.

A secondary treatment of superabsorber polymers using reactive, surface-crosslinked compounds (alkylene carbonates) to increase the liquid absorption capability under pressure has been described in DE-A-40 20 780.

The EP 0,233,067 describes water-absorbing resins crosslinked at their surface, obtained by reacting a super-absorbent polymer powder with an aluminum compound. A mixture of water and diols is used as treatment solution, which is intended to render the use of lower alcohols as solvents unnecessary. Preferably, 100 parts of crosslinker solution is applied on 100 to 300 parts of absorber. According to the examples, the reaction with the aluminum component takes place at room temperature. The diols (e.g., polyethylene glycol 400 and 2000, 1,3-butanediol or 1,5-pentanediol) added to the water reaction medium serve to prevent aggregation of the superabsorber during the treatment with such large amounts of aqueous treatment solution used therein. The solvent is removed in a subsequent drying operation at 100° C. The polymers thus treated have an insufficient level of properties, with improvement of the absorption capability under pressure not being achieved. Furthermore, a treatment using large amounts of treatment solution is not economically feasible in modern, continuously operating processes.

WO 96/05234 describes a process for the production of super-absorbing polymers, according to which a crosslinked layer is formed at the surface of the absorber particles containing at least 10 wt.-% of water by reacting a reactive, hydrophilic polymer or a reactive organometallic compound with an at least bifunctional crosslinker below 100° C. The polymer products are said to have a well-balanced correlation of absorption, gel strength and permeability, the measured values having been determined according to extremely poor criteria of evaluation. Thus, for example, the absorption and permeability have been determined without any pressure load. One drawback in this well-known process is the use of solvents and toxically critical crosslinking reagents such as polyimines, alkoxylated silicone or titanium compounds, and epoxides which are mentioned as being preferred.

An improvement in the properties of permeability and liquid conveyance is achieved in WO 95/22356 and WO 97/12575 by appropriately treating commercially available superabsorber products with aminopolymers in organic solvents. In addition to using toxicologically critical polyamines and polyimines, a serious drawback of the process described therein is the use of large amounts of organic solvents required in the treatment of the polymers. Industrial production is excluded by the safety aspect and cost associated therewith. In addition to the toxicological risk of these treatment agents, their tendency to decompose under the high temperatures of secondary crosslinking must also be taken into account which, among other things, can be seen in a yellow discoloration of the absorber particles.

The state of the art as described above does not provide any indication that a dramatic augmentation in the permeability properties is also possible in this secondary crosslinking stage, while retaining high retention capacity and capability of absorbing liquids under pressure.

It was therefore the object of the present invention to provide superabsorbing polymers which, as a combination of properties, not only have high absorbing capacity under pressure but also the normally contrary properties of high retention capability and good permeability in combination, i.e., a level of combined properties where, in addition to a retention value of at least $\geq 25$ g/g, an SFC value of at least $30 \times 10^{-7}$, preferably at least $50 \times 10^{-7}$ cm$^3 \cdot$s/g is present. In particular, it was the object to provide superabsorbing polymers which particularly would be suitable for use in very thin diaper constructions having a very high percentage of superabsorber. In particular, polymers having retention values of $\geq 25$ g/g and permeability values SFC of $>70 \times 10^{-7}$ cm$^3 \cdot$s/g are required in this case.

It was another object of the invention to find production processes for these superabsorbing polymers that would be easy, economically and safely feasible, provide constant product quality and wherein, in particular, low amounts of solvent are used, and organic solvents are avoided as far as possible. In addition, these processes should be feasible without the use of toxicologically critical substances.

The object of the invention is accomplished by providing a powdered polymer product which has been subjected to secondary crosslinking at its surface, and which absorbs water, aqueous or serous fluids, as well as blood, and is constituted of a) 55-99.9 wt.-%, preferably 70-90 wt.-% of polymerized, ethylenically unsaturated monomers which contain acid groups and are neutralized to at least 25 mole-%,
b) 0-40 wt.-%, preferably 0-20 wt.-% of polymerized, ethylenically unsaturated monomers copolymerizable with a),
c) 0.1-5.0 wt.-%, preferably 0.1-3 wt.-% of one or more polymerized crosslinking agents,
d) 0-30 wt.-%, preferably 0-5 wt.-% of a water-soluble polymer, the sum of the weight amounts a) through d) always being 100 wt.-%,
characterized in that the polymer product has been treated with
e) 0.01-5 wt.-%, relative to the polymer product, of an organic surface secondary crosslinking agent, with the exception of polyols, in the form of an aqueous solution, and
f) 0.001-1.0 wt.-%, relative to the polymer product, of a cation as a salt in the form of an aqueous solution.

Surprisingly, a superabsorber resin with significantly improved permeability properties and high retention capability is obtained by coating a particulate absorber resin with an aqueous solution of an organic crosslinking agent, with the exception of polyols, which has reacted with molecular groups near the surface, preferably with carboxyl groups, in the presence of a cation of a salt component, preferably with heating at 40 to 300° C.

Quite unexpectedly, the aqueous solution of the inventive combination of secondary crosslinker components provides the desired result, namely, superabsorber resins having high retention capability even under pressure and, at the same time, excellent permeability properties. Successive, separate use of an aqueous solution of the organic secondary crosslinking agent and an aqueous solution of the salt with heating in each case does not result in comparably good product characteristics.

The sole use of organic secondary crosslinking agents such as alkylene carbonates in aqueous solution results in products having high retention capacity, high gel strength and high absorption capability under pressure. However, a significant increase of permeability in the swollen state can only be achieved by a correspondingly higher crosslinking level of the polymers during polymerization, or by more intensive secondary crosslinking (increased amounts of secondary crosslinking agent or more severe conditions) and an associated loss of retention capacity.

Likewise, sole secondary crosslinking using high positive charge density cations will not result in polymer products having the desired combination of properties. In particular, satisfactory values of liquid absorption under pressure and good permeability properties cannot be achieved. As a consequence, treating superabsorber polymers with multivalent cations only can only increase the rate of liquid absorption. An improvement of pressure stability or even liquid conveyance properties in the swollen state is not achieved.

According to the invention, organic, at least bifunctional compounds reacting with the surface COOH groups of the polymer product are preferably used as organic secondary crosslinker component e), with the exception of polyols.

For example, these are alkylene carbonates, preferably having $C_2$-$C_{10}$ and more preferably $C_2$-$C_6$ in a ring, such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, or 1,3-dioxepan-1-one, 1,3-dioxolane, 1,3-dioxane, with 1,3-dioxolan-2-one or 4-methyl-1,3-dioxolan-2-one being preferred.

Furthermore, aminoalcohols, preferably aliphatic aminoalcohols preferably having $C_2$-$C_{10}$, such as diethanolamine, triethanolamine may be used as secondary crosslinker component e). Other suitable organic secondary crosslinker compounds which, however, must be regarded as critical due to their toxicological potential, are: polyepoxides such as polyepoxide ethers or esters of polyfunctional, preferably bifunctional polyols or carboxylic acids, e.g., ethylene glycol diglycidyl ether, polyethylene glycol diglycidyl ether, glycerol polyglycidyl ether, polyglycerol polyglycidyl ether, propylene glycol diglycidyl ether, polypropylene glycol diglycidyl ether, neopentyl glycol diglycidyl ether, pentaerythritol polyglycidyl ether, hexanediol diglycidyl ether, trimethylolpropane polyglycidyl ether, sorbitol polyglycidyl ether, phthalic acid diglycidyl ester, adipic acid diglycidyl ester, 1,4-phenylenebis(2-oxazoline), glycidol; polyisocyanates, preferably diisocyanates such as toluene-2,4-diisocyanate and hexamethylene diisocyanate; haloepoxides such as epichloro- and epibromohydrin and α-methylepichlorohydrin, aliphatic polyamine compounds such as ethylenediamine, diethylenetriamine, triethylenetetramine, polyallylamine, or polyethyleneimine. Polyoxazoline compounds such as 1,2-ethylenebisoxazoline may also be used as secondary crosslinker compounds.

The organic secondary crosslinker component or the mixtures thereof are employed in amounts of 0.01-5 wt.-%, preferably 0.1-2.5 wt.-%, and more preferably 0.5-1.5 wt.-%, relative to the polymer product to be crosslinked at its surface.

According to the invention, aqueous solutions of salts are preferably used as component f) to crosslink the carboxylate groups near the surface, the anions of which are chloride, bromide, sulfate, carbonate, nitrate, phosphate, or organic anions such as acetate and lactate. The cations preferably are derived from uni- or multivalent cations, the univalent ones preferably from alkali metals such as potassium, sodium, lithium, with lithium being preferred. Bivalent cations used according to the invention are derived from zinc, beryllium, alkaline earth metals such as magnesium, calcium, strontium, with magnesium being preferred. Other examples of polyvalent cations which may be used according to the invention are cations of aluminum, iron, chromium, manganese, titanium, zirconium, and other transition metals, as well as double salts of these cations, or mixtures of the above-mentioned salts. It is preferred to use aluminum salts and alums and their various hydrates, such as $AlCl_3 \times 6H_2O$, $NaAl(SO_4)_2 \times 12H_2O$, $KAl(SO_4)_2 \times 12H_2O$, or $Al_2(SO_4)_3 \times 14\text{-}18H_2O$. It is particularly preferred to use $Al_2(SO_4)_3$ and the hydrates thereof. Calculated relative to the cation, the salt component is employed in amounts of from 0.001 to 1.0 wt.-%, preferably 0.005 to 0.5 wt.-%, and more preferably 0.01 to 0.2 wt.-%, relative to the polymer product.

The water-absorbing polymer product to be surface-crosslinked is obtained by polymerizing a) 55-99.9 wt.-% of a monounsaturated monomer having acid groups, where monomers containing carboxyl groups are preferred, e.g., acrylic acid, methacrylic acid, 2-acrylamido-2-methylpropanesulfonic acid, or mixtures of these monomers. Preferably, at least 50% and more preferably at least 75% of the acid groups are carboxyl groups. The acid groups are neutralized to at least 25 mole-%, i.e., they are present as sodium, potassium or ammonium salts. The degree of neutralization preferably is at least 50 mole-%. Particularly preferred is a polymer product obtained by polymerization, in the presence of crosslinkers, of acrylic acid or methacrylic acid, the carboxyl groups of which have been neutralized to 50-80 mole-%.

From 0 to 40 wt.-% of ethylenically unsaturated monomers copolymerizable with a), such as acrylamide, methacrylamide, hydroxyethyl acrylate, dimethylaminoalkyl (meth) acrylate, dimethylaminopropylacrylamide, or acrylamidopropyltrimethylammonium chloride may be used as other monomers b) in the production of the absorbent polymer products. Monomers in excess of 40 wt.-% might deteriorate the swelling capability of the polymer products.

All those compounds bearing at least two ethylenically unsaturated double bonds or one ethylenically unsaturated double bond and one functional group reactive towards the acid groups of the monomers a) or multiple functional groups reactive towards acid groups may be used as crosslinker component c) present during the polymerization of a) and b). As examples may be mentioned: aliphatic amides such as methylenebisacryl- or -methacrylamide, or ethylenebisacrylamide, and also, aliphatic esters of polyols or alkoxylated polyols with ethylenically unsaturated acids, such as di(meth) acrylates or tri(meth)acrylates of butanediol or ethylene glycol, polyglycols, trimethylolpropane, di- and triacrylate esters of trimethylolpropane preferably alkoxylated with from 1 to 30 mol of alkylene oxide, preferably ethoxylated, acrylate and methacrylate esters of glycerol and pentaerythritol and of glycerol and pentaerythritol preferably ethoxylated with from 1 to 30 mol of ethylene oxide, and also, allyl compounds such as allyl (meth)acrylate, alkoxylated allyl (meth)acrylate reacted preferably with from 1 to 30 mol of ethylene oxide, triallyl cyanurate, triallyl isocyanurate, maleic acid diallyl ester, polyallyl esters, tetraallyloxyethane, triallylamine, tetraallylethylenediamine, allyl esters of phosphoric acid or phosphorous acid, and also, crosslinkable monomers such as N-methylol compounds of unsaturated amides like methacrylamide or acrylamide and the ethers derived therefrom. Mixtures of the above-mentioned crosslinkers may also be used. The percentage of crosslinking comonomers is from 0.1 to 5 wt.-%, preferably from 0.01 to 3.0 wt.-%, relative to the total amount of monomers.

From 0 to 30 wt.-% of water-soluble polymer products, such as partially or completely saponified poly(vinyl alcohol), polyvinylpyrrolidone, starch or starch derivatives, polyglycols, or poly(acrylic acids) may be included as water-soluble polymers d) in the absorbent polymer products according to the invention, preferably incorporated by polymerization. The molecular weight of these polymers is not critical as long as they are soluble in water. Preferred water-soluble polymers are starch and poly(vinyl alcohol). The preferred content of these water-soluble polymers in the absorbent polymer product of the invention is around 1-5 wt.-%, preferably 0-5 wt.-%, relative to the total amount of components a) through d). The water-soluble polymers, preferably synthetic ones such as poly(vinyl alcohol), may also serve as grafting basis for the monomers to be polymerized.

Conventional initiators such as azo or peroxo compounds, redox systems or UV initiators (sensitizers) are used to initiate the free-radical polymerization.

Preferably, the polymer products of the invention are produced according to two methods:

According to the first method, the partially neutralized monomer a), preferably acrylic acid, is converted to a gel by means of free-radical polymerization in aqueous solution and in the presence of crosslinkers and optionally other components, which gel is subsequently crushed, dried, milled, and screened to the desired particle size. Such a solution polymerization may be conducted in a continuous or batchwise fashion. The state of the art includes a broad spectrum of possible variants with respect to concentration conditions, temperatures, type and amount of initiators. Typical processes have been described in the publications U.S. Pat. No. 4,286,082, DE 27 06 135, and U.S. Pat. No. 4,076,663, the disclosures of which are hereby incorporated by reference.

Inverse suspension and emulsion polymerization may also be used to produce the products of the invention. According to these processes, an aqueous, partially neutralized solution of the monomers a), preferably acrylic acid, is dispersed in a hydrophobic organic solvent using protective colloids and/or emulsifiers, and the polymerization is initiated using free-radical initiators. The crosslinkers are either dissolved in the monomer solution and metered together with same or added separately and optionally during the polymerization. Optionally, a water-soluble polymer d) as a grafting basis is added via the monomer solution or by directly placing in the oil phase. Subsequently, the water is removed azeotropically from the mixture, and the polymer product is filtrated and optionally dried. Crosslinking may be effected by incorporating a polyfunctional crosslinker via polymerization, which is dissolved in the monomer solution, and/or by reacting suitable crosslinking agents with functional groups of the polymer during the polymerization steps. For example, these processes have been described in U.S. Pat. No. 4,340,706, DE 37 13 601, DE 28 40 010, and WO 96/05234, the disclosures of which are hereby incorporated by reference.

The polymer gel is dried to a water content of 0.5-25 wt.-%, preferably 1-10 wt.-%, and more preferably 1-8 wt.-%, at temperatures normally ranging from 100-200° C.

There are no particular limitations regarding the particle shape of the absorbent polymer products according to the invention. The polymer product may be in the form of beads obtained by inverse suspension polymerization, or in the form of irregularly shaped particles derived from drying and powdering the gel mass from solution polymerization. The particle size normally is below 3000 μm, preferably between 20 and 2000 μm, and more preferably between 150 and 850 μm.

The secondary crosslinker components according to the invention are applied in the form of their aqueous solutions. Suitable solvents are water and optionally, polar water-miscible organic solvents such as acetone, methanol, ethanol, or 2-propanol, or mixtures thereof. With respect to the solvent component, the term "aqueous solution" in the meaning of the invention indicates that other organic solvents may also be included in addition to water. The concentration of each secondary crosslinker component in the aqueous solvent may vary within wide limits, ranging from 1-80 wt.-%, preferably from 5 to 65 wt.-%, and more preferably from 10 to 40 wt.-%. The preferred solvent for the organic secondary crosslinking agent and/or the salt component is water which is used in an amount of from 0.5 to 10 wt.-%, preferably from 0.75 to 5 wt.-%, and more preferably from 1.0 to 4 wt.-%, relative to the polymer product.

If the organic secondary crosslinker and the salt component are present in an aqueous solution, the soluble quantities of both components may be limited by salting-out effects and have to be adapted in accordance with the composition. Because the amount of organic solvents must be held as low as possible for safety reasons in order to avoid explosions, a stable mixed phase of water/organic solvent/organic secondary crosslinker compound/salt component cannot be achieved at any concentration of compound. For example, a preferred solution consists of 1.5-3 parts by weight of water, 0.5-1 parts by weight of organic secondary crosslinker compound, and 0.4-0.6 parts by weight of an inorganic salt. Conventionally, the total amount of solvent employed ranges from 0.5-12 wt.-%, preferably from 1 to 7 wt.-%, and more preferably from 1 to 5 wt.-%, relative to the polymer product.

In addition to water and the above-mentioned organic solvents, other solubilizers such as inorganic or organic acids or complexing agents may also be used in order to reduce the amounts of liquid applied on the polymer product.

Depending on the solubility of both components e) and f), the solution is heated to 20-100° C., preferably 20-60° C. prior to application on the polymer product. Separate, yet simultaneous metering of a solution of the organic secondary crosslinker and a solution of the salt component is also possible if homogeneous distribution of both components on the polymer product is ensured and the material is subjected to a thermal subsequent treatment. Preferably, one single solution is applied on the polymer product, wherein both components are dissolved.

The secondary crosslinker solution should be mixed thoroughly with the polymer particles. Suitable mixing units for applying the secondary crosslinker solution are, e.g., Patterson-Kelley mixers, DRAIS turbulence mixers, Lödige mixers, Ruberg mixers, screw mixers, pan mixers, and fluid-bed mixers, as well as continuously operated vertical mixers wherein the polymer powder is mixed at a rapid frequency using rotating knives (Schugi mixer). It is also possible to coat the polymer product in the course of a particular processing step during the production of the polymer product. To this end, the process of inverse suspension polymerization is particularly suited.

Once the secondary crosslinker solution has been mixed with the polymer particles, the secondary crosslinking reaction preferably is performed at temperatures ranging from 40° C. to 300° C., preferably from 80° C. to 250° C., and more preferably from 160° C. to 210° C. The optimum time period for additional heating can easily be determined for each single type of crosslinker in just a few tests and is limited by that point where the desired pattern of properties of the superabsorber is destroyed as a result of heat damage. The thermal treatment may be carried out in usual dryers or ovens; as examples may be mentioned: rotary-tube dryers, fluid-bed dryers, disc dryers, blade dryers, or infrared dryers.

The polymers of the invention can be produced on an industrial scale according to well-known processes in a continuous or batchwise fashion.

The polymer products according to the invention may be used in a wide field of applications. If used in liners, diapers or in wound dressings, for example, they have the property of rapidly absorbing large amounts of menstruation blood, urine, or other body fluids. Because the agents according to the invention retain absorbed liquids even under pressure and, in addition, are capable of distributing additional liquid within the construction in their swollen state, it is particularly preferred to use them at higher concentrations, relative to the hydrophilic fibrous material such as fluff, than has been possible so far. They are suitable for use as homogeneous superabsorber layers, with zero amounts of fluff within the diaper construction, thereby enabling particularly thin diapers. Furthermore, the polymers are suitable for use in hygiene articles (incontinence articles) for adults.

The polymers according to the invention are also used in absorber articles suitable for most various purposes, e.g. by mixing with paper, fluff or synthetic fibers, or by dispersing the superabsorber between substrates made of paper, fluff or nonwoven textiles, or by processing into support materials to form a web. In addition, the polymers of the invention are used in all those cases where aqueous liquids have to be absorbed, e.g., in cable sheathings, in food packagings, in the agricultural field in plant breeding, as water reservoir, and as a vehicle for active substances involving the function of delayed release into the environment.

Surprisingly, the superabsorbers according to the invention exhibit a significant improvement in permeability, i.e., an improvement in liquid conveyance in the swollen state. Polymer products are obtained having permeability values (SFC) of up to $70 \times 10^{-7}$ cm$^3$·s/g at a retention (TB) of at least 27 g/g, and preferably such polymers having SFC values of from $>70 \times 10^{-7}$ to $\geq 150 \times 10^{-7}$ cm$^3$·s/g at a retention (TB) of at least 25 g/g. In addition to these excellent SFC and retention values, the polymers of the invention exhibit measured values of liquid absorption under pressure ($AAP_{0.7}$) of at least 18 g/g.

The products of the invention having this outstanding combination of properties comprising very high SFC values, high retention and high absorption under pressure can be produced without using toxicologically critical substances.

As can be seen from the following Examples, the secondary crosslinking according to the invention is applicable to a variety of polymer products having various chemical structures. Thus, it is no longer necessary to fall back on special crosslinker combinations, comonomers or expensive secondary treatment procedures at such an early stage as during the production of the polymer products in order to achieve an at least slightly increased permeability.

Test Methods

In order to characterize the absorbent polymer products of the invention, the retention (TB), absorption under pressure (AAP) and permeability for a 0.9% saline solution in the swollen state (SFC) are determined.

a) The retention is determined according to the tea bag method and is given as mean value of three measurements. About 200 mg of polymer product is welded in a tea bag and immersed in a 0.9% NaCl solution for 30 minutes. The tea bag is subsequently centrifuged in a centrifuge (23 cm in diameter, 1,400 rpm) for 3 minutes and weighed. A tea bag having no water-absorbing polymer is run as a blank.

$$\text{Retention} = \frac{\text{Final weight} - \text{Blank}}{\text{Initial weight}} \quad [g/g]$$

b) Liquid absorption under pressure (AAP test according to EP 0,339,461)

The absorption under pressure (pressure load 50 g/cm$^2$) is determined according to the method described in EP 0,339,461, page 7. About 0.9 g of superabsorber is weighed in a cylinder having a screen bottom. The uniformly spread superabsorber layer is loaded with a piston exerting a pressure of 50 g/cm$^2$. The previously weighed cylinder then is placed on a glass filter plate situated in a tray containing a 0.9% NaCl solution, the liquid level of which precisely corresponds to the height of the filter plate. After allowing the cylinder unit to absorb 0.9% NaCl solution for 1 hour, it is reweighed, and the AAP is calculated as follows:

$AAP$=Final weight(cylinder unit+superabsorber)−Initial weight(cylinder unit+soaked superabsorber)/Initial weight of superabsorber c) Permeability in the swollen state (SFC Test according to WO 95/22356)

0.9 g of superabsorber material is weighed in a cylinder having a screen bottom and spread carefully over the screen surface. The superabsorber material is allowed to swell in JAYCO synthetic urine [composition: 2.0 g of potassium chloride, 2.0 g sodium sulfate, 0.85 g of ammonium dihydrogen phosphate, 0.15 g of ammonium hydrogen phosphate, 0.19 g of calcium chloride, 0.23 g of magnesium chloride as anhydrous salts dissolved in 1 l of distilled water] for 1 hour against a pressure of 20 g/cm$^2$. After detecting the swelling height of the superabsorber, a 0.118 M NaCl solution is allowed to flow from a levelled reservoir vessel through the swollen gel layer at a constant hydrostatic pressure. During measurement, the swollen gel layer is covered with a special screen cylinder which ensures uniform distribution of the 0.118 M NaCl solution above the gel and constant conditions (measuring temperature 20-25° C.) during measurement with respect to the gel bed structure. The pressure acting on the swollen superabsorber still is 20 g/cm$^2$. Using a computer and a scale, the amount of liquid passing through the gel layer as a function of time is detected at intervals of 20 seconds within a time period of 10 minutes. The flow rate g/s through the swollen gel layer is determined using regression analysis with slope extrapolation and determination of the center to time t=0 of the flow rate over the minutes 2-10. The SFC value (K) is calculated as follows:

$$K = \frac{F_s(t=0) \times L_0}{r \times A \times \Delta P} = \frac{F_s(t=0) \times L_0}{139506}$$

wherein
$F_s(t=0)$ flow rate in g/s
$L_0$ thickness of gel layer in cm
r density of NaCl solution (1.003 g/cm$^3$)
A area of upper side of gel layer in the measuring cylinder (28.27 cm$^2$)
$\Delta P$ hydrostatic pressure resting on gel layer (4920 dyne/cm$^2$)
K SFC value [cm$^3 \cdot$s$\cdot$g$^{-1}$]

Formal addition of the figures from tea bag retention and the SFC value illustrates the abrupt increase of this combination of properties in the polymer products of the invention as compared to non-treated superabsorber powder or to products subjected to surface secondary crosslinking according to well-known methods. In the products according to the invention, said figure is not achieved by a high contribution of one of these two values (e.g., a high TB retention value and a low SFC value or vice versa).

EXAMPLES

In the Examples and Comparative Examples, each powder employed in the surface treatment of secondary crosslinking was screened to a particle size of from 150 μm to 850 μm.

Example 1

A polyacrylic acid obtained by solution polymerization, crosslinked with 0.7 wt.-% polyethylene glycol diacrylate, relative to acrylic acid, and present to 70 mole-% neutralized as sodium salt, was screened to a powder having a particle size of 150-850 μm (powder A) after drying and milling. 100 g of powder A was mixed with a solution of 1 g of 1,3-dioxolan-2-one, 3 g of water and 0.5 g of aluminum sulfate 18-hydrate with vigorous stirring and subsequently heated for 30 minutes in an oven heated to 180° C.

For comparison, 100 g of powder A was mixed with a solution of 1 g of 1,3-dioxolan-2-one and 3 g of water and subsequently heated for 30 minutes in an oven heated to 180° C. Comparative Example 1, according to DE 40 20 780).

For further comparison, 100 g of powder A was mixed with a solution of 3 g of water and 0.5 g of aluminum sulfate 18-hydrate and subsequently heated for 30 minutes in an oven heated to 180° C. (Comparative Example 2).

| Product | TB [g/g] | AAP$_{0.7}$ [g/g] | SFC [10$^{-7}$ cm$^3 \cdot$ s/g] | TB + SFC |
|---|---|---|---|---|
| Powder A | 33.5 | 8.5 | 0 | 33.5 |
| Example 1 | 29.0 | 23.5 | 70 | 99 |
| Comparative Example 1 | 29.0 | 24.5 | 15 | 43 |
| Comparative Example 2 | 32.5 | 11 | 0 | 32.5 |

Examples 2-6

Five powdered polyacrylic acids free-radically polymerized with varying amounts of polyethylene glycol diacrylate (powders B, C, D, E and F, each 100 g) and present to 70 mole-% as sodium salt, were screened to 150-850 μm after drying and milling, and mixed with a solution of 1 g of 1,3-dioxolan-2-one, 3 g of water and 0.5 g of aluminum sulfate 18-hydrate with vigorous stirring and subsequently heated for 30 minutes in an oven heated to 180° C.

| Product | TB [g/g] | Crosslinker Wt.-%/AA* | AAP$_{0.7}$ [g/g] | SFC [10$^{-7}$ cm$^3 \cdot$ s/g] | TB + SFC |
|---|---|---|---|---|---|
| Powder B | 30 | 1.1 | 12 | 0 | 30 |
| Example 2 | 26.5 | | 22.5 | 110 | 136.5 |
| Powder C | 32.5 | 0.8 | 10 | 0 | 32.5 |
| Example 3 | 29 | | 23.5 | 65 | 94 |
| Powder D | 35 | 0.6 | 11.5 | 0 | 35 |
| Example 4 | 30 | | 23 | 55 | 78 |

-continued

| Product | TB [g/g] | Crosslinker Wt.-%/AA* | AAP$_{0.7}$ [g/g] | SFC [$10^{-7}$ cm$^3 \cdot$ s/g] | TB + SFC |
|---|---|---|---|---|---|
| Powder E | 29 | 1.15 | 12 | 0 | 29 |
| Example 5 | 25.5 | | 24 | 150 | 179 |
| Powder F | 38 | 0.45 | 9 | 0 | 38 |
| Example 6 | 31 | | 24.5 | 45 | 76 |

Acrylic acid

Examples 7-11

5 crosslinked polyacrylic acids (powders E-I) were obtained using a production process wherein the content of acrylic acid (AA), which had been neutralized to 70 mole-%, in the aqueous monomer solution was varied (22-30 wt.-%, see Table), and crosslinking was effected using 0.7 wt.-%, relative to acrylic acid, of a mixture of the two crosslinkers triallylamine and polyethylene glycol diacrylate. Following drying and milling of the polymer product, screening to a particle size of 150-850 μm was effected, and 100 g of each powder
a) was mixed with a solution of 1 g of 1,3-dioxolan-2-one, 2.5 g of water and 0.5 g of aluminum sulfate 14-hydrate with vigorous stirring and subsequently heated for 60 minutes in an oven heated to 175° C. (Examples 7-11), or
b) was mixed with a solution of 1 g of 1,3-dioxolan-2-one and 3 g of water with vigorous stirring and subsequently heated for 60 minutes in an oven heated to 175° C. Comparative Example 3-7).

| Product | Wt.-% AA | TB [g/g] | AAP$_{0.7}$ [g/g] | SFC [$10^{-7}$ cm$^3 \cdot$ s/g] | TB + SFC |
|---|---|---|---|---|---|
| Powder E | 30 | 36.5 | | | |
| Example 7 | | 30 | 23.5 | 40 | 70 |
| Comp. Ex. 3 | | 30 | 24 | 22 | 52 |
| Powder F | 28 | 36 | | | |
| Example 8 | | 29.5 | 24.5 | 52 | 81.5 |
| Comp. Ex. 4 | | 30 | 25.5 | 25 | 55 |
| Powder G | 26 | 35.5 | | | |
| Example 9 | | 29 | 25 | 62 | 91 |
| Comp. Ex. 5 | | 30 | 25 | 15 | 45 |
| Powder H | 24 | 36 | | | |
| Example 10 | | 29.5 | 24 | 60 | 89.5 |
| Comp. Ex. 6 | | 30 | 24.5 | 25 | 55 |
| Powder I | 22 | 35 | | | |
| Example 11 | | 29.5 | 25.5 | 88 | 117.5 |
| Comp. Ex. 7 | | 30 | 25.5 | 24 | 54 |

Comparative Examples 8-13

20 g of the polymer powders (I) and (M), Favor® SXM 6860 (see Comparative Example 14), are heated with the following solutions/dispersions at 68° C. for 1 hour. Following cooling, the polymer is filtrated off and dried for 1 hour at 80° C. in a drying oven (cf., U.S. Pat. No. 4,043,952).
Powder (I)+
a) 0.7 g of zinc acetate in 60 g of methanol/water (90:10) (Comparative Example 8);
b) 0.18 g of basic aluminum acetate (aluminum hydroxide acetate) in 60 g of methanol (Comparative Example 9);
c) 0.1 g of Al$_2$(SO$_4$)$_3$×14H$_2$O in 60 g of methanol/water (90:10) (Comparative Example 10).
Powder (M) (Favor® SXM 6860)+
a) 0.7 g of zinc acetate in 60 g of methanol/water (90:10) (Comparative Example 11);
b) 0.18 g of basic aluminum acetate (aluminum hydroxide acetate) in 60 g of methanol (Comparative Example 12);
c) 0.1 g of Al$_2$(SO$_4$)$_3$×14H$_2$O in 60 g of methanol/water (90:10) (Comparative Example 13).

| Product | TB [g/g] | AAP$_{0.7}$ [g/g] | SFC [$10^{-7}$ cm$^3 \cdot$ s/g] | TB + SFC |
|---|---|---|---|---|
| Comparative Example 8 | 31.5 | 8 | 0 | 31.5 |
| Comparative Example 9 | 32 | 8 | 0 | 32 |
| Comparative Example 10 | 31 | 9 | 0 | 31 |
| Comparative Example 11 | 30.5 | 22 | 4 | 34.5 |
| Comparative Example 12 | 31 | 22 | 5 | 36 |
| Comparative Example 13 | 31 | 22 | 5 | 36 |
| Example 9 | 29 | 25 | 62 | 91 |

Comparative Example 14

100 g of Favor® SXM 6860 (commercial product by the company Stockhausen GmbH & Co., secondary surface-crosslinked polyacrylate) was mixed with a solution of 2.5 g of water and 0.5 g of aluminum sulfate 14-hydrate with vigorous stirring and subsequently heated for 30 minutes in an oven heated to 180° C.

| Product | TB [g/g] | AAP$_{0.7}$ [g/g] | SFC [$10^{-7}$ cm$^3 \cdot$ s/g] | TB + SFC |
|---|---|---|---|---|
| Powder M | 31.5 | 25.5 | 5 | 36.5 |
| Comparative Example 14 | 27 | 21.5 | 15 | 42 |

Examples 12-13

100 g each of powdered native wax corn starch (Cerestar SS of 4201) or polyacrylic acid containing poly(vinyl alcohol) (Mowiol® 5/88), present to 70 mole-% neutralized (powder N, 5% starch and powder 0, 3, 5% PVA)
a) were mixed with a solution of 1 g of 1,3-dioxolan-2-one, 2.5 g of water and 0.5 g of aluminum sulfate 14-hydrate with vigorous stirring and subsequently heated for 90 minutes in an oven heated to 170° C. (Examples 12 and 13);
b) were mixed with a solution of 1 g of 1,3-dioxolan-2-one and 3 g of water with vigorous stirring and subsequently heated for 30 minutes in an oven heated to 180° C. (Comparative Example 15 and 16).

| Product | TB [g/g] | AAP$_{0.7}$ [g/g] | SFC [$10^{-7}$ cm$^3 \cdot$ s/g] | TB + SFC |
|---|---|---|---|---|
| Powder N | 28 | | | |
| Example 12 | 24 | 22.5 | 115 | 139 |
| Comparative Example 15 | 24 | 23 | 38 | 62 |
| Powder O | 36 | | | |
| Example 13 | 30 | 23 | 51 | 81 |
| Comparative Example 16 | 30 | 24.5 | 20 | 50 |

Example 14

100 g of a crosslinked powdered copolymer of acrylic acid and 2 wt.-% of a methoxypolyethyleneglycol monomethacrylic acid ester (17EO) (powder P), wherein the acrylic acid was present to 70 mole-% as sodium salt, was mixed with a solution of 1 g of 1,3-dioxolan-2-one, 2.5 g of water and 0.5 g of aluminum sulfate 14-hydrate with vigorous stirring and subsequently heated for 60 minutes in an oven heated to 175° C.

For comparison, 100 g of powder was mixed with a solution of 1 g of 1,3-dioxolan-2-one and 3 g of water and subsequently heated for 60 minutes in an oven heated to 175° C. (Comparative Example 17).

| Product | TB [g/g] | $AAP_{0.7}$ [g/g] | SFC $[10^{-7} cm^3 \cdot s/g]$ | TB + SFC |
|---|---|---|---|---|
| Powder P | 35 | | | |
| Example 14 | 28.5 | 24 | 100 | 128.5 |
| Comparative Example 17 | 28 | 25 | 25 | 53 |

Examples 15-17

A polyacrylic acid obtained by free-radical solution polymerization (content of polyethylene glycol diacrylate as bifunctional crosslinker: 0.8 wt.-%, 0.7 wt.-%, and 1.1 wt.-%) and present to 70 mole-% neutralized as sodium salt, was screened to 150-850 μm (powder C, powder Q, powder S) after drying and milling. Each one of these powders is fed continuously at 80 kg/h into a blade mixer and mixed with 4 wt.-% of a solution of 1,3-dioxolan-2-one, water, and aluminum sulfate 18-hydrate (1 part/2.5 parts/0.5 parts). The treatment solution is applied finely dispersed in the mixer, using a two-fluid nozzle.

For thermal treatment, 80 kg/h of the mixture is continuously metered into a dryer equipped with disc-shaped rotating mixing elements heated to 186° C. by means of steam. Thereafter, the mixture is cooled with air in a fluid bed.

| Product | TB [g/g] | $AAP_{0.7}$ [g/g] | SFC $[10^{-7} cm^3 \cdot s/g]$ | TB + SFC |
|---|---|---|---|---|
| Powder C | 32.5 | 10 | 0 | 32.5 |
| Example 15 | 28.0 | 24.0 | 112 | 140 |
| Example 16 | 23.5 | 21.5 | 188 | 211.5 |
| Example 17 | 30 | 23.5 | 55 | 85 |

Example 18

100 g of a powdered, crosslinked polyacrylic acid (powder C) present to 70 mole-% neutralized as sodium salt was screened to 150-850 μm after drying and milling and mixed with a solution of 1 g of 1,3-dioxolan-2-one, 3 g of water and 0.7 g of aluminum chloride 6-hydrate with vigorous stirring and subsequently heated for 30 minutes in an oven heated to 180° C.

| Product | TB [g/g] | $AAP_{0.7}$ [g/g] | SFC $[10^{-7} cm^3 \cdot s/g]$ | TB + SFC |
|---|---|---|---|---|
| Powder C | 32.5 | 10 | 0 | 32.5 |
| Example 18 | 29.5 | 23.0 | 62 | 91.5 |

Example 19

100 g of a powdered, crosslinked polyacrylic acid (powder C) present to 70 mole-% neutralized as sodium salt was screened to 150-850 μm after drying and milling and mixed with a solution of 1 g of 1,3-dioxolan-2-one, 3 g of water and 0.7 g of ferric chloride 6-hydrate with vigorous stirring and subsequently heated for 30 minutes in an oven heated to 180° C.

| | TB [g/g] | $AAP_{0.7}$ [g/g] | SFC $[10^{-7} cm^3 \cdot s/g]$ | TB + SFC |
|---|---|---|---|---|
| Powder C | 32.5 | 10 | 0 | 32.5 |
| Example 19 | 29 | 22.5 | 46 | 75 |

Examples 20 and 21

100 g of a powdered, crosslinked polyacrylic acid (powder T) present to 70 mole-% neutralized as sodium salt was screened to 150-850 μm after drying and milling and mixed with a solution of 1 g of 1,3-dioxolan-2-one, 3 g of water and 0.1 g of calcium acetate hydrate (Example 20) or magnesium acetate 4-hydrate (Example 21) with vigorous stirring and subsequently heated for 30 minutes in an oven heated to 185° C.

| | TB [g/g] | $AAP_{0.7}$ [g/g] | SFC $[10^{-7} cm^3 \cdot s/g]$ | TB + SFC |
|---|---|---|---|---|
| Powder T | 31.5 | 10 | 0 | 31.5 |
| Example 20 | 28.5 | 23.5 | 40 | 68.5 |
| Example 21 | 29.0 | 24 | 42 | 71 |

Examples 22-27

Two powdered polyacrylic acids crosslinked to different levels (powders A and C, respectively, 100 g) and present to 70 mole-% neutralized as sodium salt were screened to 150-850 μm after drying and milling and mixed with a solution of 1,3-dioxolan-2-one, water and aluminum sulfate 18-hydrate in amounts as specified in the Table with vigorous stirring and subsequently heated in an oven at a temperature over a period of time as indicated.

| Product | $Al_2(SO_4)_3$** [g] | EC* [g] | $H_2O$ [g] | TB [g/g] | $AAP_{0.7}$ [g/g] | SFC [$10^{-7}$ cm$^3 \cdot$ s/g] | TB + SFC | T/t [° C./min] |
|---|---|---|---|---|---|---|---|---|
| Powder A | | | | 33.5 | 9 | 0 | 33.5 | |
| Example 22 | 0.4 | 1 | 2.25 | 29 | 23 | 62 | 91 | 175/60 |
| Example 23 | 0.45 | 0.75 | 2.5 | 29 | 22.5 | 65 | 94 | 180/40 |
| Example 24 | 0.75 | 0.75 | 2.5 | 29.5 | 22 | 121 | 150.5 | 180/30 |
| Powder C | | | | 32.5 | 10 | 0 | 32.5 | |
| Example 25 | 0.3 | 1 | 2.5 | 31 | 23.5 | 72 | 103 | 180/30 |
| Example 26 | 0.5 | 1 | 1.0 | 30 | 23 | 94 | 124 | 170/60 |
| Example 27 | 0.8 | 0.7 | 2.2 | 27 | 21 | 150 | 177 | 180/30 |

*1,3-Dioxolan-2-one
**$Al_2(SO_4)_3 \times 18 H_2O$

Examples 28 and 29

100 g at a time of a powdered crosslinked polyacrylic acid (powder U) present to 70 mole-% neutralized as sodium salt was screened to 150-850 μm after drying and milling and mixed with solutions having compositions as specified in the Table with vigorous stirring and subsequently heated in an oven according to the conditions indicated below:

| Product | $Al_2(SO_4)_3$** [g] | EC* [g] | $H_2O$ [g] | TB [g/g] | $AAP_{0.7}$ [g/g] | SFC [$10^{-7}$ cm$^3 \cdot$ s/g] | TB + SFC | T/t [° C./min] |
|---|---|---|---|---|---|---|---|---|
| Powder U | | | | 31 | 11 | 0 | 30 | |
| Example 28 | 0.5 | 0.5 | 3 | 28 | 23.5 | 43 | 71 | 180/30 |
| Example 29 | 0.5 | 0.5 | 3 | 28 | 23 | 33 | 61 | 120/30 |
| Comp. Ex. 18 | | 0.5 | 3 | 28.5 | 24 | 12 | 40.5 | 180/30 |
| Comp. Ex. 19 | | 0.5 | 3 | 28 | 24 | 9 | 37 | 120/30 |

*Ethylene glycol diglycidyl ether
**$Al_2(SO_4)_3 \times 18 H_2O$

The Examples show a significant improvement in the permeability of the polymer products of the invention in their swollen state, characterized by the SFC value. Despite high permeability, the other two relevant parameters, i.e., tea bag retention and absorption of liquid under pressure ($AAP_{0.7}$) are on a high level. It has also been demonstrated that an appropriate combination of properties comprising high retention capability, good absorption of liquid under pressure and high permeability in the swollen state can only be achieved by a treatment using a combination of organic secondary crosslinker and an inorganic salt component such as aluminum sulfate, aluminum chloride, ferric chloride, magnesium or calcium acetate with heating of the coated polymer product. The sole use of salt component (Comparative Examples 2 and 8-10) or organic secondary crosslinker (Comparative Examples 1, 3-7, and 15-17) does not result in the desired pattern of properties. Additional treatment with an aluminum salt of a polymer product which already has been subjected to surface secondary crosslinking will not result in the desired significant improvement of permeability (Comparative Examples 11 to 14). Rather, a deterioration of the retention capability and liquid absorption capability under pressure is to be noted. The surface treatments described in the Comparative Examples and taken from the patents specified in each case do not even nearly result in superabsorbers that would be comparable to the products of the invention. Moreover, when coating the polymer products using large amounts of aqueous solutions or organic solvents, serious problems will arise with respect to the feasibility of the process (massive aggregation of material, and large amounts of organic vapors to be removed).

The invention claimed is:

1. A superabsorber particulate composition having a surface which has been subjected to secondary crosslinking at its surface, comprising a polymer comprising
   a) from about 55 to about 99.9 wt % of polymerized, ethylenically unsaturated monomers comprising acrylic acid and are neutralized to 50-80 mole %,
   b) from 0 to about 40 wt % of polymerized, ethylenically unsaturated monomers copolymerizable with a),
   c) from about 0.1 to about 5.0 wt % of one or more polymerized crosslinkers,
   d) from 0 to about 30 wt % of a water soluble polymer,
   wherein the sum of the weight amounts a) through d) is 100 wt % and wherein the polymer is formed into a particulate superabsorber polymer product having a particle size from about 20 μm to 2000 μm, wherein the particulate superabsorber polymer product has been crosslinked on the surface thereof with an aqueous combination consisting of
   e) from about 1 to about 2 wt %, relative to the polymer product, of an organic surface secondary crosslinking agent consisting of 1,3-dioxolan-2-one, with the exception of polyols, and
   f) from about 0.3 to about 1 wt %, relative to the polymer product, of a compound selected from aluminum sulfate 14-hydrate, aluminum sulfate 18-hydrate, aluminum chloride 6-hydrate, ferric chloride, calcium acetate hydrate, or magnesium acetate 4-hydrate, to form a treated particulate superabsorber polymer, and the treated particulate superabsorber polymer has been subjected to surface secondary crosslinking wherein the surface secondary crosslinking reaction excludes polyols and is performed at temperatures from about 160° C. to about 210° C. to form the superabsorber particulate composition, wherein the amount of water used for the treatment of the particulate superabsorber polymer product with the an aqueous combination consisting of the organic surface secondary crosslinking agent consisting of 1,3-dioxolan-2-one of e) and the compound selected from aluminum sulfate 14-hydrate, aluminum sulfate 18-hydrate, aluminum chloride 6-hydrate, ferric chloride, calcium acetate hydrate, or magnesium acetate 4-hydrate of f) is from about 0.5 to about 10 wt % relative to the particulate superabsorber polymer product, wherein the superabsorber particulate composition has a permeability as measured by the saline flow conductivity test, SFC, of from about $40 \times 10^{-7}$ cm$^3$ s/g to about $150 \times 10^{-7}$ cm$^3$ s/g; and a retention as measured by the tea bag test, TB, of from about 23.5 g/g to about 40 g/g and a AAP$_{0.7}$ of from about 22.5 to about 25.5 g/g as measured by the liquid absorption under pressure at 0.7 psi.

2. The superabsorber particulate composition of claim 1, wherein component f) is present in an amount of from about 0.3 to about 0.7 wt %.

3. A process for producing the superabsorber composition according to claim 1, wherein a mixture of a) 55-99.9 wt.-% of ethylenically unsaturated monomers comprising acrylic acid and are neutralized to 50-80 mole %, b) from 0 to about 40 wt % of ethylenically unsaturated monomers copolymerizable with a), c) from about 0.1 to about 5.0 wt % of one or more crosslinker compounds, d) from 0 to about 30 wt % of a water-soluble polymer, the sum of components a) through d) being 100 wt %, is subjected to free-radical polymerization, optionally crushed, dried, powdered, screened, and that the polymer powder is treated with e) from about 1 to about 2 wt %, relative to the polymer product, of an alkylene carbonate selected from 1,3-dioxolan-2-one, in the form of an aqueous solution, and f) from about 0.3 to about 1 wt %, relative to the superabsorber composition, of a compound selected from aluminum sulfate 14-hydrate or aluminum sulfate 18-hydrate in the form of an aqueous solution, wherein secondary crosslinking of the polymer powder is effected with intense mixing of the aqueous solutions of components e) and f), which are present together or separately, with the superabsorber polymer powder and wherein the surface secondary crosslinking reaction is performed at temperatures from about 160° C. to about 210° C.
wherein the superabsorber particulate composition has a permeability as measured by the saline flow conductivity test, SFC, of from about $40 \times 10^{-7}$ cm$^3$ s/g to about $150 \times 10^{-7}$ cm$^3$ s/g; and a retention as measured by the tea bag test, TB, of from about 23.5 g/g to about 35 g/g and a AAP$_{0.7}$ of from about 22.5 to about 25.5 g/g as measured by the liquid absorption under pressure at 0.7 psi.

4. The process according to claim 3 wherein the polymer has a moisture content of the superabsorber composition is from about 0.5 to about 25 wt %.

5. The process according to claim 3 wherein the polymer has a particle size of the superabsorber composition is from about 150 to about 850 microns.

6. A superabsorber particulate composition which has been subjected to secondary crosslinking at its surface, comprising a polymer consisting of
 a) from about 55 to about 99.9 wt % of polymerized, ethylenically unsaturated monomers comprising acrylic acid and are neutralized to 50-80 mole %,
 b) from 0 to about 40 wt % of polymerized, ethylenically unsaturated monomers copolymerizable with a),
 c) from about 0.1 to about 5.0 wt % of one or more polymerized crosslinkers,
 d) from 0 to about 30 wt % of a water soluble polymer,
wherein the sum of the weight amounts a) through d) is 100 wt % and wherein the polymer is formed into a particulate superabsorber polymer product having a particle size from about 20 μm to 2000 μm, wherein the particulate superabsorber polymer product has been treated with
 e) from about 1 to about 2 wt %, relative to the polymer product, of an alkylene carbonate selected from 1,3-dioxolan-2-one, in the form of an aqueous solution, and
 f) from about 0.3 to about 1 wt %, relative to the polymer product, of a compound selected from aluminum sulfate 14-hydrate, aluminum sulfate 18-hydrate, aluminum chloride 6-hydrate, ferric chloride, calcium acetate hydrate, or magnesium acetate 4-hydrate and wherein the treated particulate superabsorber polymer is subjected to surface secondary crosslinking wherein the surface secondary crosslinking reaction excludes polyols and is performed at temperatures from about 160° C. to about 210° C. to form the absorbent polymer, wherein the amount of water used for the treatment of the polymer product with the alkylene carbonate of e) and the compound selected from aluminum sulfate, aluminum chloride, ferric chloride, calcium acetate or magnesium acetate of f) is from about 0.5 to about 10 wt % relative to the polymer product, wherein the superabsorber composition has a permeability as measured by the saline flow conductivity test, SFC, of about $45 \times 10^{-7}$ cm$^3$ s/g or greater; and a retention as measured by the tea bag test, TB, of about 23.5 g/g or greater.

7. A superabsorber particulate composition of claim 6, wherein component f) is present in an amount of from about 0.3 to about 0.7 wt %.

8. A superabsorber particulate composition having a surface which has been subjected to secondary crosslinking at its surface, comprising a polymer comprising
 a) from about 55 to about 99.9 wt % of polymerized, ethylenically unsaturated monomers which contain acid groups and are neutralized to at least 25 mole %,
 b) from 0 to about 40 wt % of polymerized, ethylenically unsaturated monomers copolymerized with a),
 c) from about 0.1 to about 5.0 wt % of one or more polymerized crosslinkers,
 d) from 0 to about 30 wt % of a water soluble polymer,
wherein the sum of the weight amounts a) through d) is 100 wt % and wherein the particulate superabsorber polymer product has been treated with
 e) from about 1 to about 2 wt %, relative to the polymer product, of an organic surface secondary crosslinking agent selected from 1,3-dioxolan-2-one, with the exception of polyols, and
 f) from about 0.3 to about 1 wt %, relative to the polymer product, of a compound selected from aluminum sulfate 14-hydrate, aluminum sulfate 18-hydrate, aluminum chloride 6-hydrate, ferric chloride, calcium acetate hydrate, or magnesium acetate 4-hydrate to form a treated particulate superabsorber polymer,
wherein the component f) is applied at the same time as component e) wherein the superabsorber particulate composition has a permeability as measured by the saline flow conductivity test, SFC, of from about $40 \times 10^{-7}$ cm$^3$ s/g to about $150 \times 10^{-7}$ cm$^3$ s/g.

9. The composition of claim 8, wherein the superabsorber particulate composition has a retention as measured by the tea bag test, TB, of about 23.5 g/g to about 35 g/g, and a AAP$_{0.7}$ of from about 22.5 to about 25.5 g/g as measured by the liquid absorption under pressure at 0.7 psi.

10. The composition of claim 8, wherein the surface secondary crosslinking reaction is performed at temperatures from about 160° C. to about 210° C. to form the superabsorber particulate composition.

11. The superabsorber particulate composition of claim 8, wherein component f) is present in an amount of from about 0.3 to about 0.7 wt %.

12. A process for producing the superabsorber composition according to claim 8, wherein a mixture of a) 55-99.9 wt.-% of ethylenically unsaturated monomers comprising acrylic acid and are neutralized to at least 50-80 mole %, b) from 0 to about 40 wt % of ethylenically unsaturated monomers copolymerizable with a), c) from about 0.1 to about 5.0 wt % of one or more crosslinker compounds, d) from 0 to about 30 wt % of a water-soluble polymer, the sum of components a) through d) being 100 wt %, is subjected to free-radical polymerization, optionally crushed, dried, powdered, screened, and that the polymer powder is treated with e) from about 1 to about 2 wt %, relative to the polymer product, of an alkylene carbonate selected from 1,3-dioxolan-2-one, in the form of an aqueous solution, and f) from about 0.3 to about 1 wt %, relative to the superabsorber composition, of a compound selected from aluminum sulfate 14-hydrate, aluminum sulfate 18-hydrate, aluminum chloride 6-hydrate, ferric chloride, calcium acetate hydrate, or magnesium acetate 4-hydrate in the form of an aqueous solution, wherein secondary crosslinking of the polymer powder is effected with intense mixing of the aqueous solutions of components e) and f), which are present together, with the superabsorber polymer powder and wherein the surface secondary crosslinking reaction is performed at temperatures from about 160° C. to about 210° C. wherein the superabsorber particulate composition has a permeability as measured by the saline flow conductivity test, SFC, of from about $40 \times 10^{-7}$ cm$^3$ s/g to about $150 \times 10^{-7}$ cm$^3$ s/g.

13. The process of claim 12, wherein said alkylene carbonate is ethylene carbonate and said compound of part f) is selected from aluminum sulfate 14-hydrate or aluminum sulfate 18-hydrate.

14. The process according to claim 12, wherein the moisture content of the superabsorber composition is from about 0.5 to about 25 wt %.

15. The process according to claim 12, wherein the polymer has a particle size from about 150 to about 850 microns.

16. The superabsorber particulate composition of claim 1, wherein said compound of part f) is selected from aluminum sulfate 14-hydrate or aluminum sulfate 18-hydrate.

17. The superabsorber particulate composition of claim 6, wherein said compound of part f) is selected from aluminum sulfate 14-hydrate or aluminum sulfate 18-hydrate.

* * * * *